US005187084A

United States Patent [19]

Hallsby

[11] Patent Number: 5,187,084

[45] Date of Patent: Feb. 16, 1993

[54] AUTOMATIC AIR TEMPERATURE CYCLER AND METHOD OF USE IN POLYMEROSE CHAIN REACTION

[75] Inventor: G. Anders Hallsby, Midland, Mich.

[73] Assignee: The Dow Chemical Company, Midland, Mich.

[21] Appl. No.: 542,384

[22] Filed: Jun. 22, 1990

[51] Int. Cl.[5] .................... C12P 19/34; C12M 1/38

[52] U.S. Cl. .................... 435/91; 435/287; 435/290; 435/316; 935/77; 935/78; 935/85; 935/88

[58] Field of Search .................... 435/290, 287, 91, 316, 435/172.3; 119/39; 165/60, 19, 26; 236/2; 935/77, 78, 85, 88

[56] References Cited

U.S. PATENT DOCUMENTS 4,590,158 5/1986 Eikman .................... 435/290
4,683,202 7/1987 Mullis .
4,950,608 8/1990 Kishimoto .................... 435/290

OTHER PUBLICATIONS

Rolio et al., Nucleic Acids Research, 16(7), pp. 3105-3106 (1988).
Weier et al., DNA, 7(6), pp. 441-447 (1988).
Halliday & Resnick, Fundamentals of Physics 2nd Ed. Extended pp. 358-360, 1981, John Wiley & Sons.
PGC Scientifics, p. 106 Summer '90.

*Primary Examiner*—James C. Housel
*Assistant Examiner*—William Chan
*Attorney, Agent, or Firm*—Michael G. Berkman; Thomas D. Zindricl; Ronald G. Brookens

[57] ABSTRACT

Apparatus and method for automatically developing, maintaining and repetitively duplicating a selectable predetermined temperature profile for replicating and amplifying a sequence of a stretch of DNA or RNA through use of a polymerase. An array of sample-containing vessels is supported in a reaction chamber through which a heat transfer medium in heat-exchange relationship with the vessels. The temperature of the air is controlled as a function of time to provide a preselectable sequence defining a temperature profile. The profile is cyclically repetitively reproduced to effect amplification of the desired sequence of DNA or RNA.

3 Claims, 2 Drawing Sheets

AUTOMATIC AIR TEMPERATURE CYCLER AND METHOD OF USE IN POLYMEROSE CHAIN REACTION

FIELD OF THE INVENTION AND BACKGROUND

The present invention relates to a method and apparatus which facilitates the incubation of samples at several different temperatures in a cyclical program. More particularly, the invention is directed to a process and equipment for carrying out a DNA amplification through replication of a stretch of a particular sequence of DNA or RNA, employing polymerases.

The present invention finds utility in the "polymerase chain reaction" (PCR) described, for example, in U.S. Pat. No. 4,683,202, and in which a stretch of DNA is copied using a polymerase. The general procedure there disclosed is to anneal a piece of primer DNA (oligonucleotide) at a temperature T1, to any stretch of single-stranded DNA (template) with a complimentary sequence. The DNA polymerase copies the primed piece of DNA at a temperature T2. At a temperature T3, the newly copied DNA and the primer dissociate from the template DNA, regenerating single-stranded DNA. As the cycle is caused to repeat itself, the temperature returns to T1 and the primer attaches itself to any strand of single-stranded DNA with complimentary sequence, including the ones just recently synthesized.

The procedure described produces any particular nucleic acid sequence from a given sequence of DNA in amounts which are substantially increased with reference to the amount initially present, thus facilitating detection of the nucleic acid sequences involved. Thus, the method described obviates the difficulties of detecting the presence of the DNA sequence using labeled oligonucleotide probes. The method employed in the practice of the invention effects a synthesis of the nucleic acids from an existing sequence, thus producing significantly increased amounts of a given nucleic acid of a completely specified sequence.

As described above, the replication and amplification of a particular sequence of DNA by means of the PCR technique requires utilization of a temperature profile. For efficient functioning of the PCR process, precise control of temperature at each stage of the cycle is essential. Moreover, it is important that each temperature (that is, T1 through TN) is reached as quickly as possible without exceeding the set point (that is, without "overshooting"). These goals have not been achieved or optimized in prior art techniques. One such technique is to utilize three water baths at temperatures T1, T2 and T3, between which the sample-containing tubes are cycled, either manually or automatically. In another method, electrically heated metal blocks are used. The water bath procedure has proved to be cumbersome and difficult to automate. Moreover, the heat transfer to the sample tubes has not proved to be particularly efficient. In addition, the temperature existing inside the tubes is not easily measured on a continuous basis.

The electrically heated metal block, while less cumbersome mechanically, also has problems, particularly such as related to the heat capacity of the metal. In this system, it is difficult to effect rapid changes in the temperature of the metal block, and thus the time for each cycle is unduly lengthened. In addition, the heat transfer to the liquid inside the sample tubes varies with the metal/tube surface area. Any reduction in contact area (poor fit, dust, or foreign matter between the tube and the block) causes the temperature in the tube to mismatch with that of the metal block within the treating period.

It is, therefore, a principal aim of the present invention to obviate shortcomings of prior art methods and techniques and to provide a system in which cyclical changes in temperatures are more effectively controlled, transition from one temperature to another is achieved more rapidly and more expeditiously, and in which there is a more precise correlation between the temperature of the treating environment and the temperature of the solutions in the sample-containing tubes or vials. The present invention ensures efficient heat transfer, good temperature control, and provides practical techniques for continuous monitoring of the temperature in the samples being treated.

SUMMARY OF THE INVENTION

The present invention relates to apparatus and a method for automatically developing and maintaining, and repetitively duplicating a selectable predetermined temperature profile for replicating and amplifying a sequence of a stretch of DNA through a polymerase catalyzed reaction. An array of sample-containing vessels is supported in a reaction chamber through which air at controlled temperatures is forcibly circulated as a heat-transfer medium in heat exchange relationship with the vessels. The temperature of the air is controlled as a function of time to provide a preselectable sequence defining a temperature profile. The profile is cyclically repetitively reproduced to effect replication of and amplification of the desired sequence of the DNA.

It is an important feature of the invention that the sample tube heating medium constitutes flowing air.

A related feature is that air, maintained at a maximum temperature which does not exceed the set point, is continuously blown by the tubes so that heat transfer becomes a function of air temperature and air velocity.

The method of the invention is characterized in that inlet air (at room temperature) is drawn into the reaction chamber through a fan mechanism and blown past electrical heating elements. The temperature of the heated air is controlled by a thermocouple probe which extends into the air stream.

The heating of the sample-containing vessels, in accordance with the practice of the invention, is effected by directing the heated air into contact with the sample tubes, arrayed in a housing which is shaped generally as an inverted funnel.

An important feature of the invention is the use of a temperature probe, which is inserted into a sample tube, the latter containing the same amount of liquid as contained in the sample tubes with the DNA and enzyme. This probe acts effectively to verify the temperature in the reaction tubes themselves, and this temperature is preferably recorded in a suitable chart.

It is an important feature of the invention that the temperature of the air brought into contact with the sample-containing vessels is rapidly and effectively changed and cycled, as required, through control of the electrical heating elements and the associated sensors.

A critical and advantageous feature of the present invention is that the use of air as the heat transfer medium makes it possible to effect rapid and controlled changes in the required temperature in accordance with the selected temperature profile. Objectionable lags and delays are obviated, establishing the required, stepped, temperature sequence.

The present invention is characterized in that is provides an automatic temperature cycling device which automatically varies the temperature in sample-containing vials through a continuous, repeated temperature profile utilizing flowing air as the medium for heat transfer. The transition from temperature to temperature is much more precise and controllable than in prior art procedures.

In accordance with the practice of the present invention, the PCR technique which involves the sequential steps of denaturation, oligonucleotide primer anealing, and polymerase mediated primer extension—each as a specific controlled temperature—is conducted more reliably, more efficiently, more precisely and more controllably than in prior art procedures.

It is a feature of the present invention that is enables one to carry out the necessary repeated cycles more rapidly and more reliably over many cycles of amplification.

It is a practical feature of the method and apparatus of the invention that it fulfills the need for automation and the repetitive duplication of the temperature profile necessary to practice the polymerase chain reaction as a means of markedly increasing the concentration of a particular sequence of DNA.

It is a related feature of the invention that the use of a heated gaseous medium (e.g., air), as the heat exchanging material facilitates not only rapid change of the temperature of the medium at each successive profile step, but contributes to the reliability of maintaining the desired temperature without exceeding the set point (i.e., overshooting).

The unique combination of good temperature control during continuous cycling coupled with fast response times ensures optimization of the method of the invention for amplifying the concentration of the DNA sequence.

Yet another important feature of the invention is that the apparatus involved is simple in structure, easily operated, and simply maintained.

Other and further objects, features, and advantages of the invention will be evident upon a reading of the following description considered in conjunction with the drawings.

DESCRIPTION OF THE ILLUSTRATED EMBODIMENT

In accordance with the present invention, the aims and objects are achieved by providing, for use in conjunction with a DNA polymerase for replicating a particular sequence of DNA and for amplifying the concentration thereof, a heating system having enhanced capabilities for repetitively and uninterruptedly following a predetermined temperature profile.

In substance, a critical feature of the present invention is the utilization of gas, preferably air, as a heat exchange medium to which the vials containing the DNA sequence samples are exposed during the replicating process. It is significant that the utilization of a gaseous heating medium, as taught in the present invention, renders it possible precisely, more rapidly, and more reliably to execute the required steps in the selected temperature profile. Additionally, the use of a controlled- temperature, gaseous heat exchange system obviates elevating the temperature of the samples above a deleterious set-point temperature. The heat exchange system of the present invention exhibits fast response times and excellent temperature controls during continuous and repetitive cycling as required in effectively implementing a polymerase chain reaction (PCR). Programmed temperatures are reached rapidly without overshooting, and are quickly changed and adjusted as the protocol may require.

It is an important practical feature of the method of the invention that the need to move the sample vials during the procedure, for example from bath to bath, is obviated. The apparatus used is relatively simple, and lends itself to ease of regulation, temperature sensing, and control.

Figure 1:
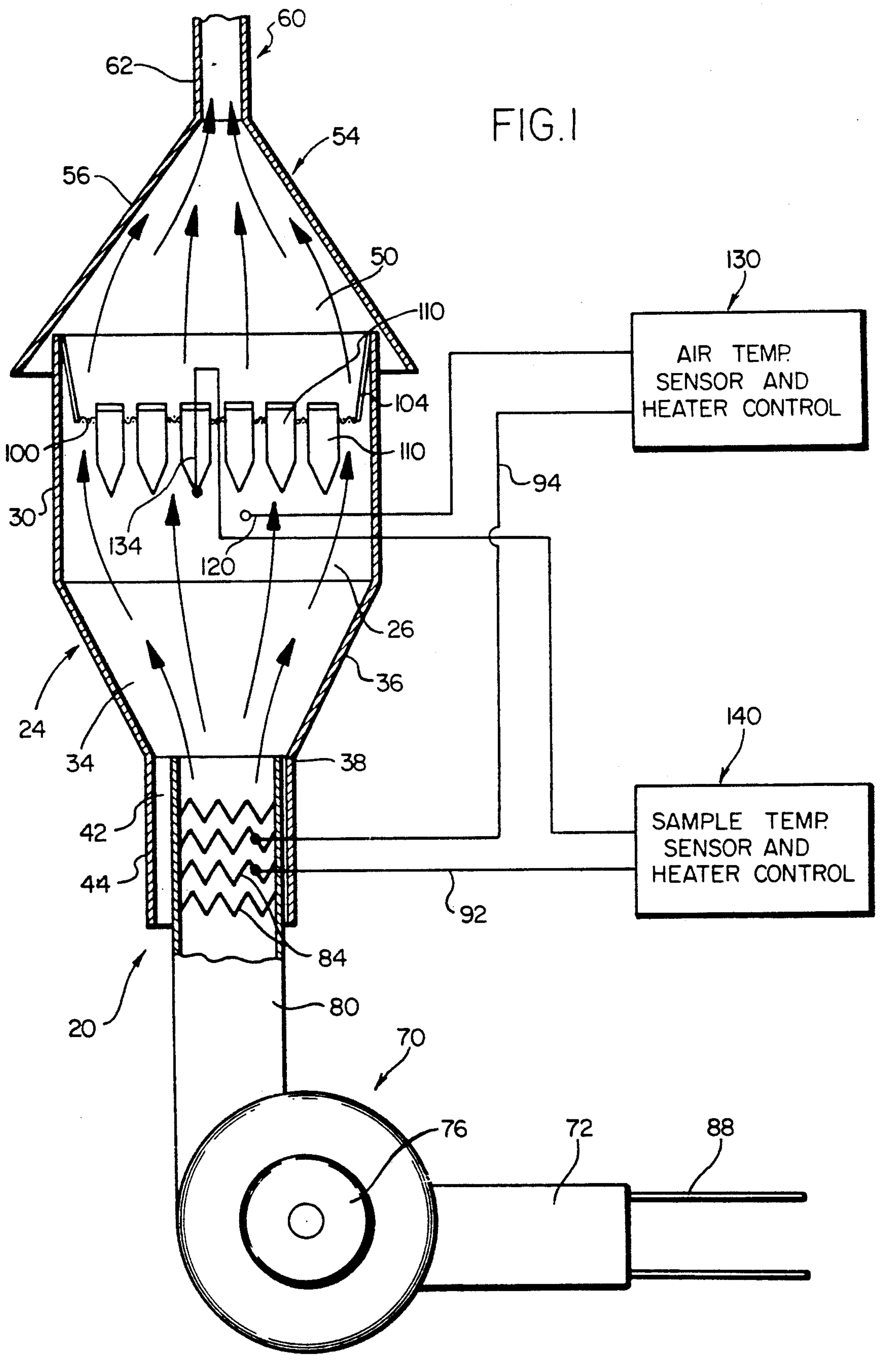
FIG. 1 is a schematic representation of the apparatus for carrying out the method of the invention embodying the features thereof, including the sensors, heaters, blowers and controls.

Referring now to the drawings, there is shown for illustrative purposes and not in any limiting sense, one embodiment of the invention incorporating the features thereof. Referring more particularly to FIG. 1, the apparatus 20, used in practicing the invention, includes a chamber or housing 24, defining a principal cavity 26 bounded by a generally cylindrical wall 30. The wall 30 is joined at its lower circular limit to a downwardly and inwardly directed frustoconical section 34 defined by a circumscribing wall 36 connected at its base 38 to a generally cylindrical inlet section 42, demarked by a circumscribing wall 44.

At its upper open end 50 the principal chamber 26 is surmounted and capped by an inverted, funnel-like cavity closure and flue 54 having an upwardly and inwardly directed wall 56 terminating in a somewhat constricted chimney or flue 60 having a circumscribing cylindrical wall 62.

In the particular preferred embodiment of the apparatus shown, the inverted funnel structure 54 overrides and is supported on the cylindrical wall 30 of the principal chamber 26.

As indicated schematically in FIG. 1, a blower and heating assembly 70, consisting of an air intake pipe 72, a blower or fan 76, and an air delivery stack 80 is positioned so as to deliver forced air into the base 42 of the reaction vessel 20, so that the air passes through the chamber and exhausts through the upwardly extending flue or stack 60. Also, as indicated schematically in FIG. 1, suitable heating elements 84 in the air delivery tube 80 heats the air which is forcibly moved through the reaction vessel 26. Suitable and conventional power leads 88, 92 and 94 deliver the required electrical power to the fan 76 and to the heating elements 84.

Figure 2:
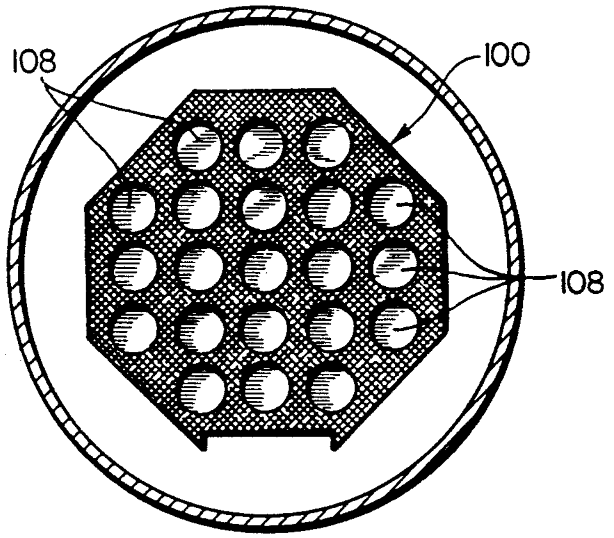
FIG. 2 is a top plan view of the rack which supports the treatment vials in the temperature controlled and programmed heater.

As indicated in FIGS. 1 and 2, a tray or rack 100 is removably supported by means of hangers 104 within the treatment or reaction cavity or chamber 26. In the specific embodiment illustrated, the rack 100 is formed with openings or slots 108 adapted to receive and support an array of tubes or sample-containing vessels 110.

The rack 100 itself may be fabricated of any suitable material such as stainless steel or an inert plastics composition. The rack 100 is supported within the principal housing or heated cavity 26 in the direct path of the heated circulating air.

As indicated schematically in FIG. 1, a temperature sensor 120 which projects into the heating chamber 26 serves to sense the temperature of the heated air and to feed that information to a controller 130 by means of which the temperature profile is set and maintained. A second temperature sensor 134, which extends into one of the tubes 110 supported in the tray or rack 100, senses the temperature in the fluid in the vessel, and feeds this information to a monitor and recorder 140. The latter is suitably coupled electrically to the heater 84 so that overheating of the liquid samples 110 is obviated.

Figure 3:
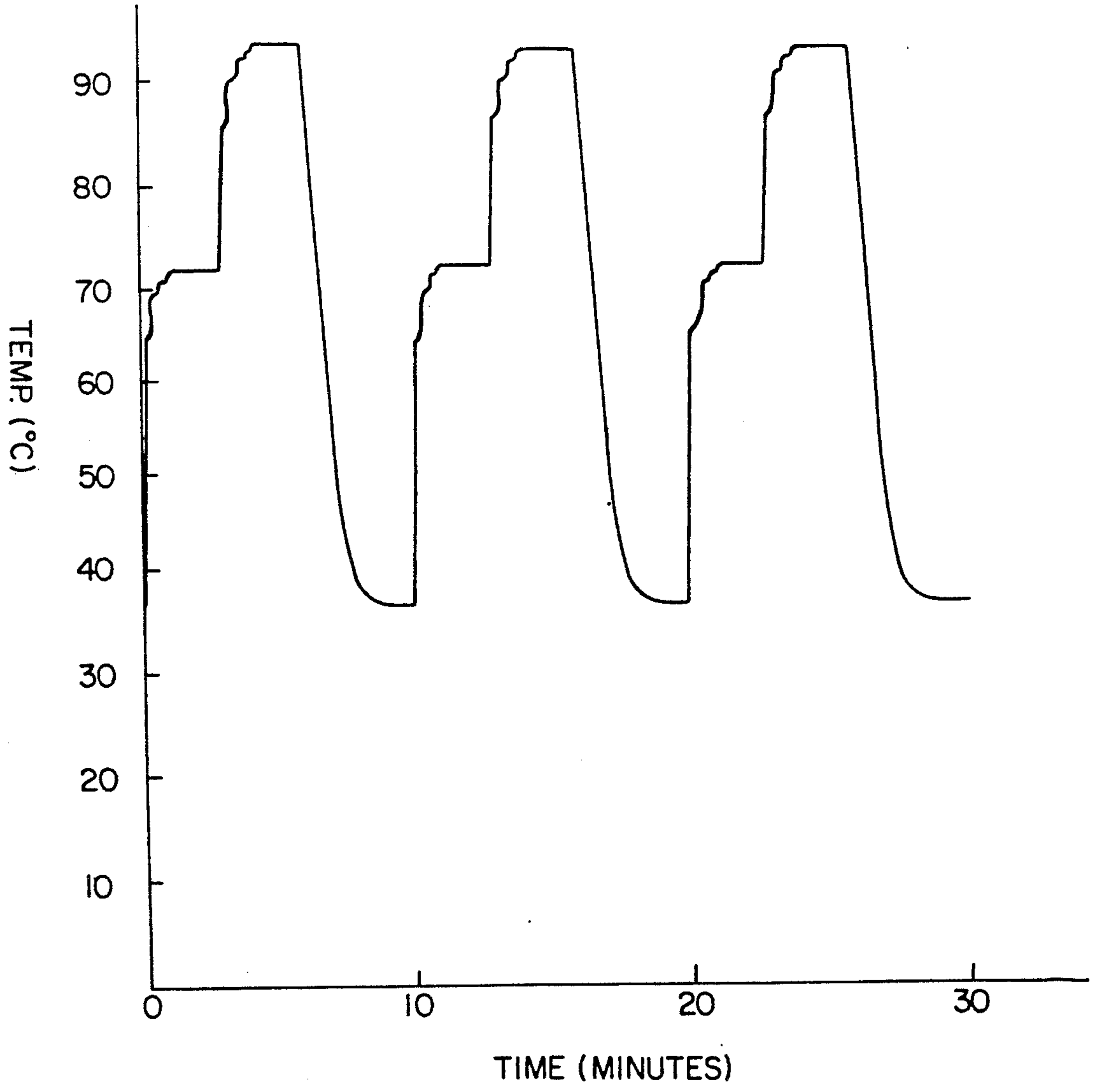
FIG. 3 is a graph depicting a typical time and temperature sequence, program or profile carried out through operation of the sample heating apparatus of the invention.

The temperature vs. time tracing representing the time and temperature profile of a stretch of DNA sample treated with the amplification and replication apparatus and method of the invention is depicted in FIG. 3, for about three cycles. The tracing, typical of what is obtained through recordings utilizing thermocouples and associated conventional equipment, shows the maintenance of a steady temperature at each temperature setting of the cycle. Also shown are the rapid changes or transitions in temperature to the next predetermined value, as called for in the selected program. FIG. 3 shows the elongation temperature for the polymerase-catalyzed DNA amplification, the rapid change to an elevated, steadily-maintained denaturation temperature, the subsequent rapid cooling to the annealing temperature, and the steady maintaining of this temperature. Finally, there is shown a completion of the cycle by rapid return to the catalyzed elongation temperature. As indicated schematically, the cycle is repeated in accordance with the particular protocol adopted.

The temperature profile is readily controllable. Each temperature in the cycle is reached precisely and exceedingly quickly without exceeding the set point. Heat transfer has been found to be excellent, and the temperature of the samples is easily monitored, on a continuous basis. Optimization in amplifying the concentration of the DNA sequence is assured.

What is claimed is:

1. In a device employing a polymerase for replicating a particular sequence of DNA or RNA and for amplifying the concentration thereof in vessels containing samples to be treated, said device includes a chamber means having means for developing and maintaining a selectable, predetermined temperature profile in said chamber means comprising a heater means, temperature cycling means, and temperature control means, the improvement comprising means for repetitively and uninterruptedly establishing and effectively controlling each of successive temperatures of said profile for a selectable time duration in a predetermined sequence of temperatures in said selectable, predetermined temperature profile, said improvement including sample treatment means comprising circulating means for distributing a heat transfer gas from ambient atmosphere in a continuous, efficient heat-exchanging mode to envelope vessels containing samples of a DNA fraction in said chamber means thereby, treating the samples thermally in sequential steps for regulated time periods defining a selectable, cyclical incubation-promoting protocol, first temperature sensor means in said chamber means for monitoring the temperature of air moving through said chamber means, second temperature sensor means including probe means projecting into one of said vessels, for sensing the temperature of the liquid samples contained in vessels containing samples to be treated, first control means functionally coupling said first temperature sensor means to said heater means for regulating said heater means to maintain a selectable program in said chamber means, consistent with said selectable, predetermined temperature profile, second control means functionally coupling said second temperature sensor means to said heater means for regulating said heater means to maintain a selectable predetermined temperature profile in said samples in said vessels corresponding to said protocol, rack means for supporting vessel-housed samples, and hanger means for supporting said rack means in said chamber means, said rack means being of a low gas flow interfering configuration to preclude impedance of and interference with circulation of heat transfer gas about the vessel-housed samples.

2. The improved device as set forth in claim 1 wherein said rack means comprises grating means for facilitating the passage of heat exchange gas therethrough.

3. In a method for replicating a particular sequence of DNA and for amplifying the concentration thereof in vessels containing samples to be treated, said method includes providing a chamber means having means for developing and maintaining a selectable, predetermined temperature profile in said chamber means comprising a heater means, temperature cycling means, and temperature control means, the improvement comprising steps of repetitively and uninterruptedly establishing and effectively controlling each of successive temperatures of said profile for a selectable time duration in a predetermined sequence of temperatures in said selectable, predetermined temperature profile, circulating a heat transfer gas in an open-ended gas throughout system in a continuous, efficient, heat-exchanging mode to envelop vessels containing samples of a DNA fraction in said chamber means then treating the samples thermally in sequential steps for regulated time periods defining a selectable, cyclical incubation-promoting protocol, positioning first sensor means in said chamber means of samples contained in the vessel thereby monitoring and controlling the temperature therein to maintain said selectable, predetermined temperature profile, and positioning second sensor means to project into a chamber-housed vessel to sense the temperature of a liquid sample contained therein, thereby monitoring and controlling the temperature to maintain a selectable, predetermined temperature profile in the sample corresponding to said protocol.

* * * * *